US008703821B2

(12) United States Patent
Song

(10) Patent No.: US 8,703,821 B2
(45) Date of Patent: Apr. 22, 2014

(54) DIALKYL ETHER DELIVERY AGENTS

(75) Inventor: Jianfeng Song, West Windsor, NJ (US)

(73) Assignee: Emisphere Technologies Inc., Roseland, NJ (US)

( * ) Notice: Subject to any disclaimer, the term of this patent is extended or adjusted under 35 U.S.C. 154(b) by 906 days.

(21) Appl. No.: 12/295,853

(22) PCT Filed: Apr. 18, 2007

(86) PCT No.: PCT/US2007/066876
§ 371 (c)(1),
(2), (4) Date: Oct. 2, 2008

(87) PCT Pub. No.: WO2007/121471
PCT Pub. Date: Oct. 25, 2007

(65) Prior Publication Data
US 2009/0092580 A1    Apr. 9, 2009

Related U.S. Application Data

(60) Provisional application No. 60/793,280, filed on Apr. 18, 2006.

(51) Int. Cl.
*A61K 31/192* (2006.01)
*C07C 59/66* (2006.01)

(52) U.S. Cl.
USPC .......................................... 514/571; 562/470

(58) Field of Classification Search
CPC ............................. A61K 31/192; C07C 59/66
See application file for complete search history.

(56) References Cited

U.S. PATENT DOCUMENTS

| | | | |
|---|---|---|---|
| 4,649,160 A * | 3/1987 | Machin | ......................... 514/652 |
| 5,401,516 A | 3/1995 | Milstein et al. | |
| 5,443,841 A | 8/1995 | Milstein et al. | |
| 5,629,020 A | 5/1997 | Leone-Bay et al. | |
| 5,643,957 A | 7/1997 | Leone-Bay et al. | |
| 5,766,633 A | 6/1998 | Milstein et al. | |
| RE35,862 E | 7/1998 | Steiner et al. | |
| 5,776,888 A | 7/1998 | Leone-Bay et al. | |
| 5,866,536 A | 2/1999 | Leone-Bay et al. | |

FOREIGN PATENT DOCUMENTS

| | | | |
|---|---|---|---|
| WO | WO 9931056 A1 * | 6/1999 | |
| WO | WO-0040203 A2 | 7/2000 | |
| WO | WO-0050386 A1 | 8/2000 | |
| WO | WO-0132130 A2 | 5/2001 | |
| WO | WO-0132596 A1 | 5/2001 | |
| WO | WO-03045306 A2 | 6/2003 | |
| WO | WO-2005/061457 A1 | 7/2005 | |
| WO | WO-2006/135316 A1 | 12/2006 | |
| WO | WO-2007/102771 A1 | 9/2007 | |

OTHER PUBLICATIONS

Abraham et al, Journal of Medicinal Chemistry, Design, Synthesis, and Testing of Potential Antisickling Agents. 4. Structure-Activity Relationships of Benzyloxy and Phenoxy Acids, 1984, 27, pp. 967-978.*
Gluud et al, Ges. Abhand. Kennt. Kohle (1917), 2, pp. 257-260, Abstract.*
International Search Report issued in PCT/US07/66876 dated Sep. 29, 2008.
Database Caplus [Online] Chemical Abstracts Service, Columbus, Ohio., US; Samizu, Kiyohiro et al: "Preparation of indolinone compounds containing azole moiety as VEGF inhibitors", XP002668803.
Database Caplus [Online] Chemical Abstracts Service. Columbus, Ohio, US; Viout, Andre et al: "Substituted benzyloxtacetic acids", XP002668804.
Chemical Abstracts Service. Columbus, Ohio, US; Ono, Satoshi et al: "Alkyl ether derivatives or salts for calcium antagonists", XP002668805.
Supplementary European Search Report issued in European Patent Application No. 07760847 on Feb. 6, 2012.

* cited by examiner

*Primary Examiner* — Paul A Zucker
(74) *Attorney, Agent, or Firm* — Blank Rome LLP

(57) ABSTRACT

The present invention provides dialkyl ether compounds and pharmaceutically acceptable salts thereof, compositions containing the same and one or more active agents, and methods of administering active agents with the same.

18 Claims, No Drawings

DIALKYL ETHER DELIVERY AGENTS

CROSS-REFERENCE TO PRIOR APPLICATIONS

This is a U.S. National Phase Application under U.S.C. §371 of International Patent Application No. PCT/US2007/066876 filed Apr. 18, 2007, which claims the benefit of U.S. Provisional Application No. 60/793,280, filed Apr. 18, 2006, The International Application published in English on Oct. 25, 2007 as WO2007/121471 under Article 21(2).

FIELD OF THE INVENTION

The present invention provides dialkyl ether delivery agent compounds and pharmaceutically acceptable salts thereof, compositions containing dialkyl ether delivery agent compounds and one or more active agents, and methods of administering an active agent comprising administering a composition that includes a dialkyl ether delivery agent compound and one or more active agents.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers. In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

A polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

International Patent Publication Nos. WO 01/32130 and WO 01/32596 disclose particular phenyl amine carboxylic acid compounds and phenoxy carboxylic acid compounds for delivering active agents. International Publication No. WO 00/50386 also discloses amine delivery agents.

International Application No. PCT/US02/36552, filed Nov. 13, 2002, published as International Application No. WO 03/045306, disclose phenoxy amine compounds and compositions for delivering active agents. Each of the above applications are hereby incorporated by reference.

However, there is still a need for simple, inexpensive delivery systems which are easily prepared and which can deliver a broad range of active agents by various routes.

SUMMARY OF THE INVENTION

The dialkyl ether delivery agents of the present invention include the following compounds:

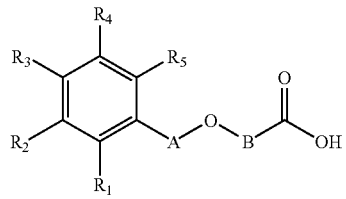

Formula I and pharmaceutically acceptable salts thereof, wherein

A is a $C_1$-$C_6$ alkylene group, preferably a straight-chained, i.e., an unsubstituted and unbranched, $C_1$-$C_6$ alkylene group;

B is a $C_1$-$C_2$ alkylene group, preferably a straight-chained, i.e., an unsubstituted and unbranched, $C_1$-$C_2$ alkylene group;

$R_1$, $R_2$, $R_3$, $R^4$ and $R_5$ are independently H, halogen, unsubstituted or substituted alkyl, unsubstituted or substituted alkenyl, unsubstituted or substituted alkoxyl, unsubstituted or substituted haloalkoxyl, hydroxyl, —C(O)$R^8$, —NO$_2$, —NR$^9$R$^{10}$, —N$^+$R$^9$R$^{10}$R$^{11}$ (R$^{12}$), carbonate, ureido, —CX$_3$, or —CN, optionally interrupted by a O, N, S, or —C(O)— group, wherein A and $R_1$ may together form a cycloalkyl group, wherein $R^8$ is independently H, $C_1$-$C_4$ alkyl, $C_2$-$C_4$ alkenyl, or —NH$_2$ group;

$R^9$, $R^{10}$, $R^{11}$, and $R^{12}$ are independently H or $C_1$-$C_{10}$ alkyl; and X is a halogen.

In a one embodiment, B is methylene and/or $R_1$, $R_2$, $R_3$, $R_4$ and $R_5$ are independently selected from hydrogen, halogen, unsubstituted or substituted alkyl, unsubstituted or substituted alkoxy or hydroxyl. In one embodiment, A and $R_1$ together form a cyclopentyl group.

In one embodiment, at least one of $R_1$, $R_2$, $R_3$, $R_4$ and $R_5$ in Formula I is methyl, chlorine, fluorine, methoxy, bromine, 1-methylethyl, butyl, ethyl, —$OC_4H_9$, or a phenyl group.

In one embodiment, at least one of $R_1$, $R_2$, $R_3$, $R_4$ and $R_5$ is interrupted by O, N, S, or —C(O)— group.

In one embodiment, A is $C_4$-$C_6$ alkylene.

Specific delivery agent compounds of the present invention include the following compounds, and pharmaceutically acceptable salts thereof:

TABLE 2

| Compound No. | Structure |
|---|---|
| 1 | 2-methylphenethyloxyacetic acid |
| 2 | 4-methylphenethyloxyacetic acid |
| 3 | 3-methylphenethyloxyacetic acid |
| 4 | 4-chlorophenethyloxyacetic acid |
| 5 | 2-chlorophenethyloxyacetic acid |
| 6 | 3-chlorophenethyloxyacetic acid |
| 7 | 4-fluorophenethyloxyacetic acid |
| 8 | 2-fluorophenethyloxyacetic acid |
| 9 | 3-fluorophenethyloxyacetic acid |
| 10 | 4-methylbenzyloxyacetic acid |
| 11 | 3-methylbenzyloxyacetic acid |
| 12 | 2-methylbenzyloxyacetic acid |
| 13 | 4-chlorobenzyloxyacetic acid |
| 14 | 3-chlorobenzyloxyacetic acid |
| 15 | 2-chlorobenzyloxyacetic acid |
| 16 | 4-fluorobenzyloxyacetic acid |
| 17 | 3-fluorobenzyloxyacetic acid |
| 18 | 2-fluorobenzyloxyacetic acid |

TABLE 2-continued

| Compound No. | Structure |
|---|---|
| 19 | 2,4,6-trimethylbenzyl-O-CH2COOH |
| 20 | 2,3,4,6-tetramethylbenzyl-O-CH2COOH |
| 21 | 2,5-dimethylbenzyl-O-CH2COOH |
| 22 | 2,4-dimethylbenzyl-O-CH2COOH |
| 23 | 3-chloro-4-methylbenzyl-O-CH2COOH |
| 24 | 2-(2,5-dimethylphenyl)ethyl-O-CH2COOH |
| 25 | 2-(3,5-dimethylphenyl)ethyl-O-CH2COOH |
| 26 | 4-phenylbutyl-O-CH2COOH |
| 27 | 2-(2-trifluoromethylphenyl)ethyl-O-CH2COOH |
| 28 | 4-(4-methoxyphenyl)butyl-O-CH2COOH |
| 29 | 3-(4-methoxyphenyl)propyl-O-CH2COOH |
| 30 | 3-(4-methylphenyl)propyl-O-CH2COOH |
| 31 | 3-(2-methylphenyl)propyl-O-CH2COOH |
| 32 | 5-phenylpentyl-O-CH2COOH |
| 33 | 2-(4-methoxyphenyl)ethyl-O-CH2COOH |
| 34 | 2-phenylethyl-O-CH2COOH |
| 35 | 3-phenylpropyl-O-CH2COOH |
| 36 | 2-(2-methoxyphenyl)ethyl-O-CH2COOH |
| 37 | 2-(2-chloro-4-fluorophenyl)ethyl-O-CH2COOH |

TABLE 2-continued

| Compound No. | Structure |
|---|---|
| 38 | 3,4-dimethoxyphenyl-(CH₂)₃-O-CH₂-COOH |
| 39 | 4-bromophenyl-(CH₂)₂-O-CH₂-COOH |
| 40 | 2-indanyl-O-CH₂-COOH |
| 41 | 1-indanyl-O-CH₂-COOH |
| 42 | 4-chlorophenyl-(CH₂)₃-O-CH₂-COOH |
| 43 | 3,4-dimethoxyphenyl-(CH₂)₂-O-CH₂-COOH |
| 44 | 4-isopropylphenyl-CH₂-O-CH₂-COOH |
| 45 | 4-butylphenyl-CH₂-O-CH₂-COOH |
| 46 | 4-ethylphenyl-CH₂-O-CH₂-COOH |
| 47 | 4-butoxyphenyl-CH₂-O-CH₂-COOH |
| 48 | 4-biphenyl-CH₂-O-CH₂-COOH |
| 49 | phenyl-(CH₂)₂-O-(CH₂)₂-COOH |
| 50 | 3-chlorophenyl-CH₂-O-(CH₂)₂-COOH |
| 51 | phenyl-(CH₂)₃-O-CH₂-COOH (propanoate) |
| 52 | 4-methylphenyl-(CH₂)₂-O-(CH₂)₂-COOH |
| 53 | 2,5-dimethylphenyl-(CH₂)₂-O-(CH₂)₂-COOH |
| 54 | 4-chlorophenyl-(CH₂)₂-O-(CH₂)₂-COOH |
| 55 | 2-chlorophenyl-(CH₂)₂-O-(CH₂)₂-COOH |
| 56 | 3-methylphenyl-(CH₂)₂-O-(CH₂)₂-COOH |

DETAILED DESCRIPTION OF THE INVENTION

Definitions

The term "delivery agent" as used herein refers to dialkyl ether compounds of the present invention, including crystalline polymorphic and amorphous forms thereof, and pharmaceutically acceptable salts of the dialkyl ether compounds of the present invention.

The term "alkylene" refers to a straight-chained, branched or substituted divalent aliphatic hydrocarbon group containing no double or triple bonds.

Unless otherwise specified, the term "substituted" refers to substitution with any one or any combination of the following subsituents: halogens, hydroxide, and $C_1$-$C_4$ alkoxy.

An "effective amount" of "an active agent or drug" is an amount of the active agent or drug (e.g., heparin, insulin, human growth hormone, etc.) which is effective to treat or prevent a condition in a living organism to whom it is administered over some period of time, e.g., provides a therapeutic effect during a desired dosing interval. Effective doses will vary, as recognized by those skilled in the art, depending on the route of administration, excipient usage, and the possibility of co-usage with other agents for treating a condition.

The term "treat", "treating", or "treated" refers to administering an active agent with the purpose to cure, heal, alleviate, prevent, relieve, alter, remedy, ameliorate, improve, or positively affect a condition (e.g., a disease), the symptoms of the condition, or the predisposition toward the condition.

An "effective amount of delivery agent" is an amount of the delivery agent which promotes the absorption of a desired amount of the active agent via any route of administration (such as those discussed in this application including, but not limited to, the oral (e.g., across a biological membrane in the gastrointestinal tract), nasal, pulmonary, dermal, vaginal, rectal, and/or ocular route).

As used herein, the term "about" means within 10% of a given value, preferably within 5%, and more preferably within 1% of a given value. Alternatively, the term "about" means that a value can fall within a scientifically acceptable error range for that type of value, which will depend on how qualitative a measurement can be given the available tools.

The phrase "pharmaceutically acceptable" refers to additives, compounds or compositions that are physiologically tolerable when administered to a mammal, including humans.

Delivery Agent Compounds

The delivery agent compounds may be in the form of the free base or pharmaceutically acceptable salts thereof. Suitable salts include, but are not limited to, organic and inorganic salts, for example ammonium, acetate salt, citrate salt, halide (preferably hydrochloride), hydroxide, sodium, sulfate, nitrate, phosphate, alkoxy, perchlorate, tetrafluoroborate, carboxylate, mesylate, fumerate, malonate, succinate, tartrate, acetate, gluconate, and maleate. Preferred salts include, but are not limited to, citrate and mesylate salts. The salts may also be solvates, including ethanol solvates, and hydrates.

In one embodiment the pharmaceutically acceptable salts of the delivery agent compounds are sodium salts, including disodium salts and solvates. In one embodiment the pharmaceutically acceptable salts of the delivery agent compounds are disodium solvates with ethanol.

Salts of the delivery agent compounds of the present invention may be prepared by methods known in the art. For example, citrate salts and mesylate salts may be prepared in ethanol, toluene and citric acid.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, acetone, methanol, and tetrahydrofuran (THF) and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent may contain a polymer conjugated to it, e.g., as described in International Publication No. WO 03/045331, which is incorporated herein by reference. For example, the delivery agent may contain a polymer conjugated to it by a linkage group selected from —NHC(O)NH—, —C(O)NH—, —NHC(O), —OOC—, —COO—, —NHC(O)O—, —OC(O)NH—, —CH$_2$NH, —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Delivery agent compounds of the present invention, particularly delivery agent compounds of formula I in which B is a methylene group, can be prepared according to the following reaction scheme, in which the first reactant is the analogous alcohol to the desired dialkyl ether:

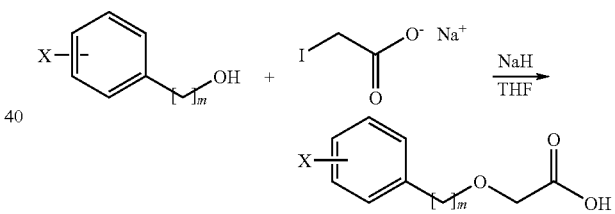

This reaction can be carried out at around 65-70° C. (see Example 1 below).

Delivery agent compounds of the present invention, particularly delivery agents in which B in formula I is an ethylene group, can be prepared according to the following reaction scheme, in which the first reactant is the analogous alcohol to the desired dialkyl ether:

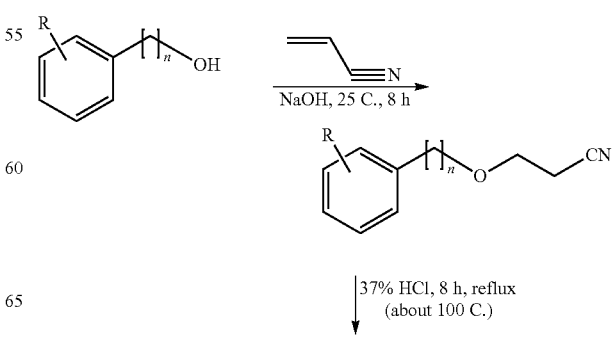

-continued

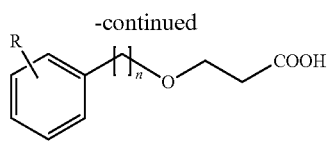

For compounds in which an oil is obtained from the above reaction schemes, a sodium salt can be obtained upon treatment with sodium trimethylsilanolate, e.g. 0.9 equivalent of sodium trimethylsilanolate.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastrointestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastrointestinal mucosa and/or are susceptible to chemical cleavage by acids and enzymes in the gastrointestinal tract; or any combination thereof.

Further examples of biologically active agents include, but are not limited to, the following, including synthetic, natural or recombinant sources thereof: amylin and amylin agonists; adrenocorticotropin; antigens; antimicrobials, including antibiotics, anti-bacterials and anti-fungal agents; non-limiting examples of antibiotics include gram-positive acting, bacteriocidal, lipopeptidal and cyclic peptidal antibiotics, such as daptomycin and analogs thereof; anti-migraine agents such as BIBM-4096BS and other calcitonin gene-related proteins antagonists, sumatriptan succinate; antivirals including but not limited to acyclovir, valacyclovir; atrial naturetic factor; argatroban; bisphosphonates, including but not limited to alendronate, clodronate, etidronate, ibandronate, incadronate, minodronate, neridronate, olpadronate, pamidronate, risedronate, tiludronate, zoledronate, EB1053, AND YH529; BIBN4096BS, i.e., (1-piperidinecarboxamide n-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R—(R*, S*)]—); calcitonin, including salmon, eel, porcine and human; cholecystokinin (CCK) and CCK agonists including CCK-8; cromolyn sodium (sodium or disodium chromoglycate); CPHPC; cyclosporine; desferrioxamine (DFO); erythropoietin; exedin and exedin agonists, including exendin-3, exendin-4; filgrastim; follicle stimulating hormone (recombinant and natural); gallium nitrate; glucagon; glucagon-like peptide 1 (GLP-1), glucagon, and glucagon-like peptide 2 (GLP-2); glucocerebrosidase; gonadotropin releasing hormone; growth hormone releasing factor; growth hormone releasing hormones; growth hormones, including human growth hormones (hGH), recombinant human growth hormones (rhGH), bovine growth hormones, and porcine growth hormones; heparin, including unfractionated heparin, heparinoids, dermatans, chondroitins, low molecular weight heparin, very low molecular weight heparin ultra low molecular weight heparin and synthetic heparins including fondiparinux; insulin, including porcine, bovine, human, and human recombinant, optionally having counter ions including zinc, sodium, calcium and ammonium; insulin-like growth factor, including IGF-1; interferons, including a (e.g., interferon alfacon-1 (available as Infergen® from InterMune, Inc. of Brisbane, Calif.)), alpha, β, omega and γ; interleukin-1; interleukin-2; interleukin-11; interleukin-21; leutinizing hormone and leutinizing hormone releasing hormone; leptin (OB protein); methyphenidate salt; monoclonal antibodies including retuxin, tnf-alpha soluble receptors; oxytocin; parathyroid hormone (PTH), including its fragments, including PTH 1-34 and PTH 1-38; peptide YY (PYY) including PYY agonists, fragment 3-36; dipeptidyl peptidase iv (DPP-4) inhibitors; prostaglandins; protease inhibitors; somatostatin; thrombopoietin; vancomycin; vasopressin; vitamins; vaccines including those against anthrax or *y. pestis*, influenza, and herpes.

Delivery Systems

The composition of the present invention comprises one or more delivery agent compounds of the present invention, and one or more active agents. In one embodiment, one or more of the delivery agent compounds, or pharmaceutically acceptable salts of these compounds, or poly amino acids or peptides of which these delivery agent compounds or salts form one or more of the units thereof, may be used as a delivery agent by mixing with the active agent prior to administration to form an administration composition.

The administration compositions may be in the form of a liquid. The solution medium may be water (for example, used in embodiments with salmon calcitonin, parathyroid hormone, and erythropoietin), 25% aqueous propylene glycol (for example, used in embodiments with heparin) and phosphate buffer (for example, used in embodiments with rhGH). Other dosing vehicles include polyethylene glycol. Dosing solutions may be prepared by mixing a solution of the delivery agent compound with a solution of the active agent, just prior to administration. Alternatively, a solution of the delivery agent compound (or active agent) may be mixed with the solid form of the active agent (or delivery agent compound). The delivery agent compound and the active agent may be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, including pH stabilizing additives. In one embodiment, the concentration of the stabilizing additives ranges between about 0.1 and 20% (w/v).

The administration compositions may alternatively be in the form of a solid, such as a tablet, capsule or particle, such as a powder or sachet. Solid dosage forms may be prepared by mixing the solid form of the compound with the solid form of the active agent. Alternatively, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone in various embodiments, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, gelatin capsules, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Preferably, an effective amount of the composition for the treatment or prevention of the desired disease or for achieving the desired physiological effect is administered. Specific indications for active agents can be found in the Physicians' Desk Reference (54th Ed., 2000, Medical Economics Company, Inc., Montvale, N.J.) and (58$^{th}$ Ed. 2004, Medical Economics Company, Inc., Montvale N.J.), which are herein incorporated by reference. Specific indications for active agents can also be found in Fauci, A S, et. al., Harrison's Principles of Internal Medicine (14$^{th}$ Ed., 1998, McGraw-Hill Health Professions Division, New York). The active agents in the table below include their analogs, fragments, mimetics, and polyethylene glycol-modified derivatives, and can be administered with delivery agents to improve the bioavailability of the active agent, as compared to administering the active agent alone.

TABLE 2

| Active Agent | Disease and Physiological Effect |
| --- | --- |
| Growth hormones (including human recombinant growth hormone and growth-hormone releasing factors and its analogs) | Growth disorders |
| Interferons, including α, β and γ. | Viral infection, including chronic cancer and multiple sclerosis |
| Interleukin-1; interleukin-2. | Viral infection; cancer |
| Insulin; Insulin-like growth factor IGF-1. | Diabetes |
| Heparin | Thrombosis; prevention of blood coagulation |
| Calcitonin. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory dysfunction (to stimulate ovulation) |
| Oxytocin | Labor dysfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |

TABLE 2-continued

| Active Agent | Disease and Physiological Effect |
|---|---|
| Cromolyn sodium; Vancomycin | Asthma; allergies |
| Desferrioxamine (DFO) | Iron overload |
| Parathyroid hormone (PTH), including its fragments. | Osteoporosis; Diseases of the bone |
| GLP-1, PYY (e.g. $PYY_{3-36}$) | Diabetes; obesity |
| Antimicrobials | Infection including gram-positive bacterial infection |
| Vitamins | Vitamin deficiencies |
| Bisphosphonates: Ibandronate, alendronate, etidronate, tiludronate, risedronate, pamidronate. | Osteoporosis; Paget's disease; Inhibits osteoclasts |
| Acyclovir | Used to treat herpes infections of the skin, lip, and genitals; herpes zoster (shingles); and chickenpox. |
| BIBN4096BS - (1-Piperidinecarboxamide. N-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R-(R*,S*)]-) | Anti-migraine; calcitonin gene- related peptide antagonist |
| Glucagon | Severe hypoglycemia |
| CPHPC | Alzheimer's Disease and diseases characterized by amyloid deposits |
| HIV Entry Inhibitors (e.g. Fuzeon) | Inhibit entry of HIV into host cells |
| Sumatriptan, almotriptan, naratriptan, rizatriptan, frovatriptan and eletriptan: (piperidinyloxy)phenyl, (piperidinyloxy)pyridinyl, (piperidinylsulfanyl)phenyl and (piperidinylsulfanyl)pyridinyl compounds | Anti-migraine serotonin agonists |
| Neuraminidase inhibitors: peramivir, zanamivir, oseltamivir, BCX-1898, BCX-1827, BCX-1989, BCX 1923, BCX 1827 and A315675; M2 inhibitors: amantadine, rimantadine; Nucleoside/Nucleotide Reverse Transcriptase Inhibitors, Non-nucleoside Reverse Transcriptase Inhibitors, Protease Inhibitors, Fusion inhibitors: thiovir, thiophosphonoformate, foscarnet, enfuviritide, zidovudine, didanosine, zalcitabine, stavudine, lamivudine, emtricitabine, abacavir, azidothymidine, tenofovir disoproxil, delavridine, efavirenz, nevirapine, ritonavir, nelfinavir mesylate, saquinvir mesylate, indinavir sulfate, amprenavir, lopinavir, lopinavir, fosamprenavir calcium, atazanavir sulfate | Antivirals |

For example, one embodiment of the present invention is a method for treating a patient having or susceptible to diabetes by administering insulin (e.g. orally administering) and at least one of the delivery agent compounds of the present invention. Other active agents, including those set forth by way of non-limiting example in the above table, can be used in conjunction with the delivery agents of the present invention.

Following administration, the active agent present in the composition or dosage unit form is taken up into the circulation. The bioavailability of the agent can be readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

Pharmaceutical Compositions

The pharmaceutical composition is preferably in solid form and may be formed into a solid dosage form. The solid dosage form can be a capsule, tablet or particle, such as a powder or sachet. The powder may be in the form of a sachet that is mixed with a liquid and administered. The solid dosage form may also be a topical delivery system, such as an ointment, cream or semi-solid. The solid dosage form contemplated may include a sustained release or controlled release system. Preferably, the solid dosage form is for oral administration.

The powder may be packed into capsules, or pressed into tablets, used in powder form, or incorporated into an ointment, cream or semi-solid. Methods for forming solid dosage forms, including solid oral dosage forms, are well known in the art.

The amount of delivery agent in the solid dosage form is a delivery effective amount and can be determined for any particular compound or biologically or chemically active agent by methods known to those skilled in the art. In one embodiment, the weight ratio of delivery agent:active ranges from about 1:1 to about 500:1, or about 1:5 or 5:1 to about 300:1. In another embodiment, the ratio of delivery agent:active may range from about 10:1 to about 200:1, or 50:1 to about 150:1. The amount of delivery agent used will vary according to the active agent, and the particular indication for which the active agent is administered.

Following administration, the active agent in the dosage unit form is taken up into circulation. The bioavailability of the active agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

The solid dosage form may include pharmaceutically acceptable additives, such as excipients, carriers, diluents, stabilizers, plasticizers, binders, glidants, disintegrants, bulking agents, lubricants, plasticizers, colorants, film formers, flavoring agents, preservatives, dosing vehicles, surfactants, and any combination of any of the foregoing. Preferably, these additives are pharmaceutically acceptable additives, such as those described in *Remington's, The Science and Practice of Pharmacy*, (Gennaro, A. R., ed., 19th edition, 1995, Mack Pub. Co.) which is hereby incorporated by reference.

Suitable binders include, but are not limited to, starch, gelatin, sugars (such as sucrose, molasses and lactose), dibasic calcium phosphate dihydrate, natural and synthetic gums (such as acacia, sodium alginate, carboxymethyl cellulose, methyl cellulose, polyvinylpyrrolidone, polyethylene glycol, ethylcellulose, and waxes.

Suitable glidants include, but are not limited to, talc, and silicon dioxide (silica) (e.g, fumed silica and colloidal silicon dioxide).

Suitable disintegrants include, but are not limited to, starches, sodium starch glycolate, croscarmellose sodium, crospovidone, clays, celluloses (such as purified cellullose, methylcellulose, sodium carboxymethyl cellulose), alginates, pregelatinized corn starches, and gums (such as agar, guar, locust bean, karaya, pectin and tragacanth gums). A preferred disintegrant is sodium starch glycolate.

Suitable bulking agents include, but are not limited to, starches (such as rice starch), microcrystalline cellulose, lactose (e.g., lactose monohydrate), sucrose, dextrose, mannitol, calcium sulfate, dicalcium sulfate, and tricalcium sulfate.

Suitable lubricants include, but are not limited to, stearic acid, stearates (such as calcium stearate and magnesium stearate), talc, boric acid, sodium benzoate, sodium acetate, sodium fumarate, sodium chloride, polyethylene glycol, hydrogenated cottonseed, and castor oils.

Suitable surfactants include, but are not limited to, sodium lauryl sulfate, hydroxylated soy lecithin, polysorbates, and block copolymers of propylene oxide and ethylene oxide.

EXAMPLES

The following examples illustrate the invention without limitation. All parts are given by weight unless otherwise indicated.

Proton nuclear magnetic resonance ($^1$H NMR) analyses for the compounds listed below were conducted on a 300 MHz Bruker spectrometer or a 400 MHz JEOL spectrometer.

Example 1

Preparation of Compounds

1A. Preparation of the Free Acid of (2,4,6-Trimethyl-benzyloxy)-acetic acid (Compound 19)

(2,4,6-Trimethyl-phenyl)-methanol (4.50 g, 30 mmol) was introduced to the suspension of sodium hydride (95%, 0.84 g, 35 mmol) in dry THF (100 ml), under a nitrogen blanket and the reaction mixture was heated to reflux for one hour. After the reaction mixture cooled down to 25° C., sodium iodoacetate (7.28 g, 35 mmol) was added in one portion, and the reaction was heated to reflux for another two hours. The resulting precipitate was collected by filtration, and then dissolved into water (60 ml). This aqueous solution was acidified to pH 2 at 5° C. by 6N HCl to generate precipitate, which was then isolated by filtration to give pure benzyloxy acetic acid as white powder (3.2 g, 51.2%), mp 81-83°. Microanalysis for $C_{12}H_{16}O_3$ (208.26): C, 69.21, H, 7.74. found: C, 68.83, H, 7.66. $^1$H-NMR ($d_6$-DMSO): 6.82 (s, 2 arom. H); 4.50 (s, OCH$_2$CO$_2$H); 4.01, 4.02 (2s, CH$_2$O); 2.29 (s, 2 ortho-CH$_3$); 2.20 (s, para-CH$_3$).

All other compounds were prepared in a procedure analogous to that described above. Those compounds obtained as an oil were converted into sodium salt by the treatment of sodium trimethylsilanolate (0.9 equiv.).

1B. Preparation of (2-o-Tolyl-ethoxy)-acetic acid (Compound 1)

Under $N_2$, 2-methylphenethyl alcohol (4.09 g, 30 mmol) was introduced to a suspension of sodium hydride (95%, 0.84 g, 35 mmol) in dry THF (100 ml), and the reaction mixture was heated to reflux for 1 h. After the reaction mixture cooled down to 25° C., sodium iodoacatate (7.28 g, 35 mmol) was added in one portion, and the reaction was heated to reflux for another 2 h. The resulting precipitate was collected by filtration, and then dissolved into water (60 ml). This aqueous solution was acidified to pH 2 at 5° C. by 6N HCl to generate precipitate, which was then isolated by filtration to give pure acid as white powder (4.0 g, 64.0%). Mp 47-48°. Microanalysis Calc. for C11H14O3 (194.23): C, 68.02, H, 7.27. found: C, 67.87, H, 7.18. 1H-NMR (300 MHz, d6-DMSO): 7.12 (m, 4 arom. H); 4.01 (s, CH2CO$_2$H); 3.63 (t, J=7.2, —CH2CH2O—); 2.83 (t, J=7.2, —CH2CH2O—); 2.27 (s, —CH3).

Compounds 2, 4, 7, 9, 10, 12, 13, 15, 19, 20, 21, 22, 23, 24, 25, 29, 33, 35, 39, 40, 42 and 47 were made as free acids from the corresponding alcohol by the procedure of Example 1B.

1C. Preparation of Sodium (2-m-Tolyl-ethoxy)-acetate (Compound 3)

Under $N_2$, 3-methylphenethyl alcohol (4.09 g, 30 mmol) was introduced to the suspension of sodium hydride (95%, 0.84 g, 35 mmol) in dry THF (100 ml), and the reaction mixture was heated to reflux for 1 h. After the reaction mixture cooled down to 25° C., sodium iodoacatate (7.28 g, 35 mmol) was added in one portion, and the reaction was heated to reflux for another 2 h. The resulting precipitate was collected by filtration, and then dissolved into water (60 ml). After acidification to pH 2 at 5° C. by 6N HCl, the mixture was extracted with Et$_2$O (50 ml×3). The organic phase was combined and washed with water (10 ml×2) respectively. The ether extract was dried with anhydrous sodium sulfate and then concentrated to give (2-m-Tolyl-ethoxy)-acetic acid as oil (4.40 g, 22.65 mmol), which was then treated with of 1 M sodium trimethylsilanolate (22.0 ml, 22.0 mmol) to give sodium (2-m-Tolyl-ethoxy)-acetate as white powder (4.90 g, 70.9%). $^1$H-NMR (300 MHz, D2O): 7.24 (m, 1 arom. H); 7.11 (m, 3 arom. H); 3.86 (s, CH2CO2H); 3.71 (t, J=6.9, —CH2CH2O—); 2.86 (t, J=6.9, —CH2CH2O—); 2.29 (s, —CH3).

Compounds 5, 6, 8, 11, 14, 16, 17, 18, 26, 27, 28, 30, 31, 32, 34, 36, 37, 38, 41, 43, 44, 45, 46 and 48 were prepared as sodium salts by from the corresponding alcohol in a process analogous to Example 1C.

Physical data for the remaining compounds are set forth below:

Compound 2: Mp 50-52°. Micoanalysis Calc. for $C_{11}H_{14}O_3$ (194.23): C, 68.02, H, 7.27; found: C, 67.88, H, 7.36. $^1$H-NMR (300 MHz, d6-DMSO): 7.10, 7.08 (AB, $J_{AB}$=8.1, 4 arom. H); 3.99 (s, $CH_2CO_2H$); 3.63 (t, J=7.0, —$CH_2CH_2O$—); 2.78 (t, J=7.0, —$CH_2CH_2O$—); 2.26 (s, —$CH_3$).

Compound 4: Mp 51-52°. Micoanalysis Calc. for $C_{10}H_{11}ClO_3$ (214.65): C, 55.96, H, 5.17; found: C, 55.87, H, 5.27. $^1$H-NMR (300 MHz, d6-DMSO): 7.32, 7.28 (AB, $J_{AB}$=7.8, 4 arom. H); 4.00 (s, $CH_2CO_2H$); 3.67 (t, J=6.6, —$CH_2CH_2O$—); 2.82 (t, J=6.6, —$CH_2CH_2O$—).

Compound 5: $^1$H-NMR (300 MHz, $D_2O$): 7.37 (m, 1 arom. H); 7.31 (m, 1 arom. H); 7.22 (m, 2 arom. H); 3.88 (s, $CH_2CO_2H$); 3.69 (t, J=7.2, —$CH_2CH_2O$—); 3.00 (t, J=7.2, —$CH_2CH_2O$).

Compound 6: $^1$H-NMR (400 MHz, $D_2O$): 7.24 (m, 4 arom. H); 3.74 (s, $CH_2CO_2H$); 3.61 (t, J=6.8, —$CH_2CH_2O$—); 2.78 (t, J=6.8, —$CH_2CH_2O$—).

Compound 7: Mp 67-68°. Micoanalysis Calc. for $C_{10}H_{11}FO_3$ (198.20): C, 60.60, H, 5.59; found: C, 60.52, H, 5.71. $^1$H-NMR (300 MHz, d6-DMSO): 7.28 (m, 2 arom. H); 7.10 (m, 2 arom. H); 4.00 (s, $CH_2CO_2H$); 3.65 (t, J=6.9, —$CH_2CH_2O$—); 2.82 (t, J=6.9, —$CH_2CH_2O$—).

Compound 8: $^1$H-NMR (300 MHz, $D_2O$): 7.17 (m, 2 arom. H); 7.00 (m, 2 arom. H); 3.76 (s, $CH_2CO_2H$); 3.61 (t, J=6.8, —$CH_2CH_2O$—); 2.82 (t, J=6.8, —$CH_2CH_2O$).

Compound 9: Mp 36-37°. Micoanalysis Calc. for $C_{10}H_{11}FO_3$ (198.20): C, 60.60, H, 5.59; found: C, 60.55, H, 5.68. $^1$H-NMR (300 MHz, d6-DMSO): 7.31 (m, 1 arom. H); 7.10 (m, 2 arom. H); 7.01 (m, 1 arom. H); 4.00 (s, $CH_2CO_2H$); 3.68 (t, J=6.6, —$CH_2CH_2O$—); 2.85 (t, J=6.6, —$CH_2CH_2O$—).

Compound 10: Mp 44-45°. Micoanalysis Calc. for $C_{10}H_{12}O_3$ (180.21): C, 66.65, H, 6.71; found: C, 67.08, H, 6.83. $^1$H-NMR (300 MHz, d6-DMSO): 7.22, 7.15 (AB, $J_{AB}$=7.8, 4 arom. H); 4.48 (s, $CH_2CO_2H$); 4.02 (s, $CH_2O$—); 2.29 (s, —$CH_3$).

Compound 11: $^1$H-NMR (400 MHz, $D_2O$): 7.22 (m, 1 arom. H); 7.15 (m, 3 arom. H); 4.43 (s, $CH_2CO_2$); 3.82 (s, $CH_2O$—); 2.26 (s, —$CH_3$).

Compound 12: Micoanalysis Calc. for $C_{10}H_{12}O_3$ (180.21): C, 66.65, H, 6.71. found: C, 66.45, H, 6.85. $^1$H-NMR (400 MHz, d6-DMSO): 7.27 (m, 1 arom. H); 7.17 (m, 3 arom. H); 4.51 (s, $CH_2CO_2$); 4.05 (s, $CH_2O$—); 2.26 (s, —$CH_3$). $^{13}$C-NMR (100 MHz, d6-DMSO): 171.56 (—C=O); 136.33; 135.81; 129.90; 128.42; 127.70; 125.57; 70.48; 66.95; 18.33.

Compound 13: Micoanalysis Calc. for $C_9H_9ClO_3$ (200.62): C, 53.88, H, 4.52. found: C, 53.62, H, 4.11. $^1$H-NMR (400 MHz, d6-DMSO): 7.41 (m, 4 arom. H); 4.52 (s, $CH_2CO_2$); 4.06 (s, $CH_2O$—). $^{13}$C-NMR (100 MHz, d6-DMSO): 171.46 (—C=O); 136.96; 132.06; 129.39 (2 arom. C); 128.20 (2 arom. C); 71.14; 66.92.

Compound 14: $^1$H-NMR (400 MHz, $D_2O$): 7.34 (m, 1 arom. H); 7.20 (m, 3 arom. H); 4.45 (s, $CH_2CO_2$); 3.82 (s, $CH_2O$—). $^{13}$C-NMR (100 MHz, d6-DMSO): 171.46 (—C=O); 136.96; 132.06; 129.39 (2 arom. C); 128.20 (2 arom. C); 71.14; 66.92. $^{13}$C-NMR (100 MHz, $D_2O$): 177.90 (—C=O); 139.47; 133.78; 130.18; 128.18; 128.12; 126.68; 71.81; 68.93.

Compound 15: Micoanalysis Calc. for $C_9H_9ClO_3$ (200.62): C, 53.88, H, 4.52. found: C, 53.78, H, 4.46. $^1$H-NMR (400 MHz, d6-DMSO): 7.54 (m, 1 arom. H); 7.42 (m, 1 arom. H); 7.33 (m, 3 arom. H); 4.62 (s, $CH_2CO_2$); 4.13 (s, $CH_2O$—). $^{13}$C-NMR (100 MHz, d6-DMSO): 171.40 (—C=O); 135.40; 131.78; 129.28; 129.20; 129.04; 127.15; 69.12; 67.21.

Compound 16: $^1$H-NMR (400 MHz, $D_2O$): 7.28 (m, 2 arom. H); 7.00 (m, 2 arom. H); 4.65 (s, $CH_2CO_2$); 3.84 (s, $CH_2O$—).

Compound 17: $^1$H-NMR (400 MHz, $D_2O$): 7.27 (m, 1 arom. H); 7.04 (m, 3 arom. H); 4.45 (s, $CH_2CO_2$); 3.82 (s, $CH_2O$—).

Compound 18: $^1$H-NMR (400 MHz, $D_2O$): 7.28 (m, 2 arom. H); 7.07 (m, 2 arom. H); 4.53 (s, $CH_2CO_2$); 3.82 (s, $CH_2O$—).

Compound 19: Mp 81-83°. Micoanalysis Calc. for $C_{12}H_{16}O_3$ (208.26): C, 69.21, H, 7.74; found: C, 68.83, H, 7.66. $^1$H-NMR (300 MHz, d6-DMSO): 6.82 (s, 2 arom. H); 4.50 (s, $CH_2CO_2$); 4.01 (s, $CH_2O$—); 2.29 (s, 2 meta-$CH_3$); 2.20 (s, para-$CH_3$).

Compound 20: Mp 103-105°. Micoanalysis Calc. for $C_{13}H_{18}O_3$ (222.29): C, 70.24, H, 8.16. found: C, 69.91, H, 8.33. $^1$H-NMR (300 MHz, d6-DMSO): 6.93 (s, 1 arom. H); 4.57 (s, $CH_2CO_2$); 4.07 (s, $CH_2O$—); 2.21 (s, 2-$CH_3$); 2.18 (s, 2-$CH_3$).

Compound 21: Mp 74-75°. Micoanalysis Calc. for $C_{11}H_{14}O_3$ (194.23): C, 68.02, H, 7.27; found: C, 68.06, H, 7.43. $^1$H-NMR (300 MHz, d6-DMSO): 7.12 (s, 1 arom. H); 7.03 (m, 2 arom. H); 4.49 (s, $CH_2CO_2$); 4.06 (s, $CH_2O$—); 2.26 (s, 1-$CH_3$); 2.23 (s, 1-$CH_3$).

Compound 22: Mp 54-56°. Micoanalysis Calc. for $C_{11}H_{14}O_3$ (194.23): C, 68.02, H, 7.27; found: C, 67.89, H, 7.20. $^1$H-NMR (300 MHz, d6-DMSO): 7.16 (m, 1 arom. H); 6.98 (m, 2 arom. H); 4.48 (s, $CH_2CO_2$); 4.03 (s, $CH_2O$—); 2.25 (s, 2-$CH_3$).

Compound 23: Mp 53-54°. Micoanalysis Calc. for $C_{10}H_{11}ClO_3$ (214.65): C, 55.96, H, 5.17. found: C, 55.92, H, 5.36. $^1$H-NMR (300 MHz, d6-DMSO): 7.34 (m, 2 arom. H); 7.19 (m, 1 aroma. H); 4.49 (s, $CH_2CO_2$); 4.06 (s, $CH_2O$—); 2.32 (s, —$CH_3$).

Compound 24: Mp 42-43°. Micoanalysis Calc. for $C_{12}H_{16}O_3$ (208.26): C, 69.21, H, 7.74; found: C, 69.18, H, 7.93. $^1$H-NMR (300 MHz, d6-DMSO): 7.00 (m, 2 arom. H); 6.89 (m, 1 arom. H); 4.01 (s, $CH_2CO_2H$); 3.61 (t, J=7.3, —$CH_2CH_2O$—); 2.78 (t, J=7.3, —$CH_2CH_2O$—); 2.22 (s, 2 —$CH_3$).

Compound 25: Mp 50-51°. Micoanalysis Calc. for $C_{12}H_{16}O_3$ (208.26): C, 69.21, H, 7.74; found: C, 69.24, H, 7.88. $^1$H-NMR (300 MHz, d6-DMSO): 6.83 (m, 3 arom. H); 4.00 (s, $CH_2CO_2H$); 3.63 (t, J=7.2, —$CH_2CH_2O$—); 2.50 (t, J=7.2, —$CH_2CH_2O$—); 2.22 (s, 2 —$CH_3$).

Compound 26: 1H-NMR (300 MHz, $D_2O$): 7.29 (m, 5 arom. H); 3.85 (s, $CH_2CO_2$); 3.50 (t, J=6.6, $CH_2O$—); 2.63 (t, J=7.0, $C_6H_5$—$CH_2$—); 1.62 (m, —$CH_2CH_2CH_2O$—).

Compound 27: 1H-NMR (400 MHz, $D_2O$): 7.61 (m, 1 arom. H); 7.43 (m, 2 arom. H); 7.31 (m, 1 arom. H); 3.82 (s, $CH_2CO_2$); 3.65 (m, $CH_2CH_2O$—); 2.83 (m, $CH_2CH_2O$—).

Compound 28: $^1$H-NMR (400 MHz, $D_2O$): 7.06 (m, 2 arom. H); 6.79 (m, 2 arom. H); 3.73 (s, $CH_2CO_2$); 3.65 (s, $OCH_3$); 3.35 (m, $CH_2O$—); 2.42 (m, $C_6H_4$—$CH_2$—); 1.44 (m, —$CH_2CH_2CH_2O$—). $^{13}$C-NMR (100 MHz, $D_2O$): 178.28 (—C=O); 156.92; 135.74; 129.72 (2 arom. C); 114.05 (2 arom. C); 70.96; 69.48; 55.47; 33.86; 28.18; 27.35.

Compound 29: 1H-NMR (400 MHz, d6-DMSO): 7.02, 6.74 (AB, $J_{AB}$=8.8, 4 arom. H); 3.90 (s, $CH_2CO_2$); 3.63 (s, $OCH_3$); 3.35 (t, J=6.4, $CH_2O$—); 2.47 (t, J=7.2, $C_6H_4$—$CH_2$—); 1.68 (m, —$CH_2CH_2CH_2O$—). $^{13}$C-NMR (100 MHz, d6-DMSO): 171.76 (—C=O); 157.80; 133.57; 129.20 (2 arom. C); 113.68 (2 arom. C); 69.85; 67.44; 54.93; 30.90; 30.72.

Compound 30: 1H-NMR (400 MHz, $D_2O$): 7.11 (s, 4 arom. H); 3.80 (s, $CH_2CO_2$); 3.42 (t, J=6.4, $CH_2O$—); 2.56 (t, J=7.6, $C_6H_4$—$CH_2$—); 2.21 (s, —$CH_3$); 1.79 (m, —$CH_2CH_2CH_2O$—). $^{13}$C-NMR (100 MHz, $D_2O$): 178.28 (—C=O); 139.31; 135.99; 129.23 (2 arom. C); 128.64 (2 arom. C); 70.40; 69.57; 31.01; 30.58; 20.06.

Compound 31: 1H-NMR (400 MHz, $D_2O$): 7.25 (m, 4 arom. H); 3.92 (s, $CH_2CO_2$); 3.56 (t, J=6.4, $CH_2O$—); 2.70 (t, J=7.9, $C_6H_4$—$CH_2$—); 2.32 (s, —$CH_3$); 1.87 (m, —$CH_2CH_2CH_2O$—). $^{13}$C-NMR (100 MHz, $D_2O$): 178.28 (—C=O); 140.63; 136.69; 130.29; 129.15; 126.35; 126.22; 70.58; 69.54; 29.30; 28.88; 18.35.

Compound 32: 1H-NMR (400 MHz, $D_2O$): 6.92 (m, 5 arom. H); 3.72 (s, $CH_2CO_2$); 3.23 (t, J=6.9, $CH_2O$—); 2.70 (t, J=7.9, $C_6H_5$—$CH_2$—); 1.37 (m, 4H of $C_6H_5$—$CH_2$—$(CH_2)_3$); 1.07 (m, 2H of $C_6H_5$—$CH_2$—$(CH_2)_3$). $^{13}$C-NMR (100 MHz, $D_2O$): 177.99 (—C=O); 142.72; 128.42 (2 arom. C); 128.34 (2 arom. C); 125.68; 71.14; 69.72; 35.50; 30.95; 28.76; 25.20.

Compound 33: 1H-NMR (400 MHz, d6-DMSO): 7.05, 6.74 (AB, $J_{AB}$=8.5, 4 arom. H); 3.80 (s, $CH_2CO_2H$); 3.62 (s, $OCH_3$); 3.50 (t, J=7.2, —$CH_2CH_2O$—); 2.65 (t, J=7.2, —$CH_2CH_2O$—). $^{13}$C-NMR (100 MHz, d6-DMSO): 177.92 (—C=O); 157.59; 130.68; 129.69 (2 arom. C); 113.60 (2 arom. C); 71.35; 68.08; 54.93; 35.80.

Compound 34: 1H-NMR (400 MHz, $D_2O$): 7.23 (m, 5 arom. H); 3.89 (s, $CH_2CO_2H$); 3.67 (t, J=6.8, —$CH_2CH_2O$—); 2.82 (t, J=6.8, —$CH_2CH_2O$—). $^{13}$C-NMR (100 MHz, $D_2O$): 176.52 (—C=O); 138.89; 129.01 (2 arom. C); 128.76 (2 arom. C); 126.60; 71.84; 68.58; 35.06.

Compound 35: 1H-NMR (400 MHz, d6-DMSO): 7.20 (m, 5 arom. H); 4.00 (s, $CH_2CO_2$); 3.45 (t, J=6.4, $CH_2O$—); 2.62 (t, J=7.6, $C_6H_5$—$CH_2$—); 1.79 (m, —$CH_2CH_2CH_2O$—). $^{13}$C-NMR (100 MHz, d6-DMSO): $_{171}$.70 (—C=O); 141.74; 128.27 (2 arom. C); 128.25 (2 arom. C); 125.69; 68.84; 67.40; 30.11; 30.97.

Compound 36: 1H-NMR (400 MHz, $D_2O$): 7.29 (m, 2 arom. H); 7.01 (m, 2 arom. H); 3.91 (s, $CH_2CO_2H$); 3.86 (s, $OCH_3$); 3.73 (t, J=6.8, —$CH_2CH_2O$—); 2.93 (t, J=6.8, —$CH_2CH_2O$—). $^{13}$C-NMR (100 MHz, $D_2O$): 178.21 (—C=O); 157.40; 130.77; 128.21; 126.91; 121.15; 111.73; 70.31; 69.40; 55.74; 29.63.

Compound 37: $^1$H-NMR (400 MHz, $D_2O$): 7.21 (m, 1 arom. H); 7.08 (m, 1 arom. H); 6.91 (m, 1 arom. H); 3.78 (s, $CH_2CO_2H$); 3.60 (t, J=6.8, —$CH_2CH_2O$—); 2.88 (t, J=6.8, —$CH_2CH_2O$—).

Compound 38: $^1$H-NMR (400 MHz, $D_2O$): 6.73 (m, 2 arom. H); 6.62 (m, 1 arom. H); 3.90 (s, $CH_2CO_2$); 3.62, 3.58 (2s, 2 $OCH_3$); 3.36 (t, J=6.4, $CH_2O$—); 2.47 (t, J=7.4, $C_6H_3$—$CH_2$—); 1.70 (m, —$CH_2CH_2CH_2O$—). $^{13}$C-NMR (100 MHz, $D_2O$): 171.78 (—C=O); 148.65; 146.93; 134.24; 120.00; 112.29; 111.90; 69.88; 67.46; 55.51; 55.35; 31.23; 31.18.

Compound 39: $^1$H-NMR (400 MHz, d6-DMSO): 7.32, 7.09 (AB, $J_{AB}$=8.0, 4 arom. H); 3.76 (s, $CH_2CO_2$); 3.50 (t, J=6.8, —$CH_2CH_2O$—); 2.67 (t, J=6.8, —$CH_2CH_2O$—). $^{13}$C-NMR (100 MHz, d6-DMSO): 172.045 (—C=O); 138.55; 131.08 (2 arom. C); 130.96 (2 arom. C); 119.03; 70.57; 68.24; 34.90.

Compound 40: $^1$H-NMR (400 MHz, d6-DMSO): 7.18 (m, 2 arom. H); 7.11 (m, 2 arom. H); 4.36 (m, CH—$OCH_2$); 4.00 (s, $CH_2CO_2$); 3.05 (dd, 2H); 2.91 (dd, 2H). $^{13}$C-NMR (100 MHz, d6-DMSO): 171.76 (—C=O); 140.88 (2 arom. C); 126.29 (2 arom. C); 124.50 (2 arom. C); 79.94; 65.80; 38.90 (2 C).

Compound 41: 1H-NMR (400 MHz, $D_2O$): 7.38 (m, 1 arom. H); 7.22 (m, 3 arom. H); 4.91 (m, CH—$OCH_2$); 3.86 (s, $CH_2CO_2$); 2.91 (m, 1H); 2.70 (m, 1H); 2.18 (m, 1H); 1.99 (m, 1H). $^{13}$C-NMR (100 MHz, $D_2O$): 171.76 (—C=O); 144.95; 141.77; 129.04; 126.52; 125.52; 125.22; 83.40; 67.18; 31.58; 29.65.

Compound 42: 1H-NMR (400 MHz, d6-DMSO): 7.18, 7.11 (AB, $J_{AB}$=8.2, 4 arom. H); 4.90 (s, $CH_2CO_2$); 3.31 (t, J=6.4, $CH_2O$—); 2.49 (t, J=7.3, $C_6H_4$—$CH_2$—); 1.65 (m, —$CH_2CH_2CH_2O$—). $^{13}$C-NMR (100 MHz, d6-DMSO): 171.70 (—C=O); 140.75; 130.28; 130.18 (2 arom. C); 128.13 (2 arom. C); 69.64; 67.39; 30.01; 30.88.

Compound 43: 1H-NMR (400 MHz, $D_2O$): 6.84 (m, 5 arom. H); 3.78 (s, $CH_2CO_2$); 3.70 (s, 2 $OCH_3$); 3.60 (m, $CH_2CH_2O$—); 2.71 (m, $CH_2CH_2O$—).

Compound 44: 1 H-NMR (400 MHz, $D_2O$): 7.36 (m, 4 arom. H); 4.55 (s, $CH_2CO_2$); 3.91 (s, $CH_2O$—); 2.93 (m, $CH(CH_3)_2$); 1.22 (d, $CH(CH_3)_2$). $^{13}$C-NMR (100 MHz, $D_2O$): 178.06 (—C=O); 149.67; 134.74; 128.92 (2 arom. C); 126.79 (2 arom. C); 72.30; 68.61; 33.42; 23.31 ($CH(CH_3)_2$).

Compound 45: 1H-NMR (400 MHz, $D_2O$): 7.21 (m, 4 arom. H); 4.41 (s, $CH_2CO_2$); 3.78 (s, $CH_2O$—); 2.49 (m, $CH_2CH_2CH_2CH_3$); 1.44 (m, $CH_2CH_2CH_2CH_3$); 1.64 (m, $CH_2CH_2CH_2CH_3$); 0.75 (t, $CH_2CH_2CH_2CH_3$). $^{13}$C-NMR (100 MHz, $D_2O$): 178.07 (—C=O); 143.69; 134.49; 128.78 (4 arom. C); 72.35; 68.60; 34.58; 33.13; 21.72; 13.28.

Compound 46: 1H-NMR (400 MHz, $D_2O$): 7.22 (m, 4 arom. H); 4.42 (s, $CH_2CO_2$); 3.78 (s, $CH_2O$—); 2.52 (q, $CH_2CH_3$); 1.06 (t, $CH_2CH_3$). $^{13}$C-NMR (100 MHz, $D_2O$): 178.03 (—C=O); 145.01; 134.43; 128.88 (2 arom. C); 128.14 (2 arom. C); 72.28; 68.50; 28.02; 15.07.

Compound 47: 1H-NMR (400 MHz, d6-DMSO): 7.20, 6.87 (AB, $J_{AB}$=8.2, 4 arom. H); 4.42 (s, $CH_2CO_2$); 3.99 (s, $CH_2O$—); 3.88 (t, $OCH_2CH_2CH_2CH_3$); 1.66 (m, $OCH_2CH_2CH_2CH_3$); 1.42 (m, $OCH_2CH_2CH_2CH_3$); 0.90 (t, $OCH_2CH_2CH_2CH_3$). $^{13}$C-NMR (100 MHz, d6-DMSO): 171.73 (—C=O); 158.36; 129.67; 129.52 (2 arom. C); 114.20 (2 arom. C); 71.79; 67.17; 66.64; 30.83; 18.82; 13.74.

Compound 48: 1H-NMR (400 MHz, $D_2O$): 7.55 (m, 4 arom. H); 7.37 (m, 5 arom. H); 4.49 (s, $CH_2CO_2$); 3.82 (s, $CH_2O$—).

Example 2

Insulin Oral Delivery in Rats

Insulin (human recombinant) was obtained from ICN Biomedicals (Aurora, Ohio) as a bulk powder. To prepare stock solutions, insulin was dissolved in deionized water (pH~6.5) to obtain a concentration of 15 mg/ml. Stock solutions were kept frozen at −20° C. in 1.0-ml aliquots until used. For dosing solutions, delivery agent was dissolved in deionized water to obtain a final concentration of 200 mg/ml. The free acid form of delivery agent was converted to the sodium salt by adding one equivalent of sodium hydroxide (1.0N). Solutions were vortexed, sonicated, and heated, and if necessary, additional sodium hydroxide was added in µl quantities to achieve uniform solubility. Solutions were adjusted to a pH of 3.5-8.5 by the addition of either hydrochloric acid or sodium hydroxide. Insulin stock (typically 66.7 µls) was then added to the delivery agent solution to obtain a final concentration of 0.5 mg/ml. After solubilization and drug addition, solutions were brought to final volume by the addition of deionized water.

Insulin was administered to male, Sprague-Dawley rats either alone or in combination with a delivery agent compound by oral gavage (PO). Rats were fasted for 18-24 hours prior to dosing. For dosing, a Rusch 8 French catheter was cut to 11 cm in length and adapted to fit a 1-ml syringe. The syringe was filled with dosing solution and the catheter was wiped dry of excess solution. The catheter was inserted into the rat mouth and fed down the esophagus (10.0 cm). The dosing solution was delivered by pressing the syringe plunger while holding the rat in an upright position.

Sample Collection and Handling: Insulin

During blood sampling, rats were exposed briefly (~10 sec) to carbon dioxide until prostrate, immediately prior to each sampling time point. For blood sampling, a 77-mm capillary tube was inserted into the retroorbital sinus. Blood samples were collected prior to dosing (time 0) and at 15, 30, 45, and 60 minutes after dosing. Samples were collected into Capiject® tubes (Terumo Corporation, Tokyo, Japan) containing a clot activator (red top, serum separator tubes). Samples were allowed to clot for ~20 min at 4° C. After clotting, samples were centrifuged at 10,000 rpm for 4 minutes at 6° C. in order to separate the serum. Serum was collected into eppendorf tubes and frozen at −20° C. until assayed.

Bioanalytical Method and Data Analysis-insulin Assay

Concentrations of insulin were quantified in rat serum using radioimmunoassay (RIA) kit from Diagnostic System Laboratories, Inc. Webster, Tex. Serum from rats was obtained internally from stock animals and used to prepare calibration standards and low and high quality control samples (LQC, HQC). The low and high quality control samples for the second curve were prepared at 30 and 150 µIU/mL, respectively. Calibration standards were prepared fresh daily and quality control samples were stored at a nominal temperature of −20° C. Concentration values (test samples) were read from the standard curve, averaged for each time point (n=5), and plotted as mean serum concentration of insulin (±SEM) versus time.

TABLE 2

| Compound No. | % Glucose $C_{min}$ (Rat) |
|---|---|
| 1 | −36.5 |
| 2 | −54.3 |
| 3 | −30.1 |
| 4 | −54.3 |
| 5 | −39.7 |
| 6 | −20.9 |
| 7 | −41.9 |
| 8 | −33.5 |
| 9 | −29.3 |
| 10 | −46.6 |
| 11 | −23.7 |
| 13 | −45.3 |
| 14 | −35.3 |
| 15 | −39.9 |
| 16 | −18.1 |
| 17 | −17.6 |
| 18 | −14.6 |
| 19 | −27.5 |
| 21 | −35.0 |
| 23 | −5.5 |
| 24 | −24.7 |
| 25 | −4.6 |
| 26 | −21.0 |
| 27 | −11.3 |
| 28 | −10.6 |
| 29 | −36.3 |
| 30 | −19.5 |
| 31 | −6.1 |
| 32 | −15.1 |
| 33 | −9.8 |
| 34 | −32.2 |
| 35 | −26.1 |
| 36 | −4.4 |
| 37 | −30.0 |
| 39 | −31.6 |

TABLE 2-continued

| Compound No. | % Glucose $C_{min}$ (Rat) |
|---|---|
| 40 | −15.8 |
| 41 | −27.8 |
| 42 | −20.4 |

Example 3

Heparin Delivery in Rats

Oral dosing solutions containing delivery agent compound and heparin sodium USP were prepared in 25% aqueous propylene glycol. Either the sodium salt of the delivery agent compound was used or the free acid was converted to the sodium salt with one equivalent of sodium hydroxide. The delivery agent compound and heparin (about 166-182 IU/mg) were mixed by vortex as dry powders. This dry mixture was dissolved in 25% v/v aqueous propylene glycol, vortexed, and placed in a sonicator (about 37° C.). The pH was adjusted to about 7 (6.5-8.5) with aqueous NaOH (2N). The dosing solution was sonicated to produce a clear solution. The final volume was adjusted to about 3.0 ml.

Male Sprague-Dawley rats were fasted for 24 hours and anesthetized with ketamine hydrochloride (88 mg/kg) intramuscularly immediately prior to dosing and again as needed to maintain anesthesia. A dosing group of five animals were administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Citrated blood samples were collected by cardiac puncture following the administration of ketamine (88 mg/kg), typically at 0.25, 0.5, 1.0 and 1.5 hours after dosing. Citrated blood samples were collected by cardiac puncture following the administration of ketamine (88 mg/kg), typically at 0.5, 1.0, 2.0, 3.0 and 4.0 hours after dosing. LMWH absorption was verified by an increase in plasma LMWH measured by the anti-Factor Xa assay CHROMOSTRATE™ Heparin anti-Xa assay (available from Organon Teknika Corporation, Durham, N.C.).

| Delivery Agent Compound | Delivery Agent Compound Dose (mg/kg) | LMWH Dose (IU/kg) | Volume Dose (ml/kg) | Mean Peak Plasma LMWH Concentration (IU/ml) ± SD |
|---|---|---|---|---|
| 2 | 300 | 100 | 3 | 1.828 |
| 19 | 300 | 100 | 3 | 0.336 |
| A* | 300 | 100 | 3 | 0.984 |

*Delivery Agent A is the monosodium salt of N-(8-[2-hydroxybenzoyl]-amino)caprylic acid

\* \* \* \* \*

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

The invention claimed is:

1. A pharmaceutical composition comprising:
 (A) a biologically active agent; and
 (B) at least one delivery agent compound having the formula

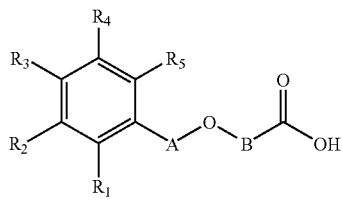

Formula I or a pharmaceutically acceptable salt thereof, wherein
 A is a $C_1$-$C_6$ alkylene group;
 B is a $C_1$-$C_2$ alkylene group;
 $R_1$, $R_2$, $R_3$, $R_4$ and $R_5$ are independently H, halogen, unsubstituted or substituted alkyl, unsubstituted or substituted alkenyl, unsubstituted or substituted alkoxyl, unsubstituted or substituted haloalkoxyl, hydroxyl, —C(O)$R^8$, —$NO_2$, —$NR^9R^{10}$, —$N^+R^9R^{10}R^{11}$ ($R^{12}$), carbonate, ureido, —$CX_3$, or —CN, optionally interrupted by a O, N, S, or —C(O)— group, wherein A and $R_1$ may together form a cycloalkyl group, wherein
 $R^8$ is independently H, $C_1$-$C_4$ alkyl, $C_2$-$C_4$ alkenyl, or —$NH_2$;
 $R^9$, $R^{10}$, $R^{11}$, and $R^{12}$ are independently H or $C_1$-$C_{10}$ alkyl; and
 X is a halogen, and
 wherein said biologically active agent is selected from: amylin and amylin agonists; adrenocorticotropin; antigens; antimicrobials, antibiotics, anti-bacterials and anti-fungal agents; anti-migraine agents; BIBM-4096BS, sumatriptan succinate; antivirals, acyclovir, valacyclovir; atrial naturetic factor; argatroban; bisphosphonates, alendronate, clodronate, etidronate, ibandronate, incadronate, minodronate, neridronate, olpadronate, pamidronate, risedronate, tiludronate, zoledronate, EB1053, AND YH529; BIBN4096BS-(1-piperidinecarboxamide. n-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dih ydro-2-oxo-3(2HO-quinazolinyl)-. [R—(R*,S*)])—); calcitonin, salmon calcitonin, eel calcitonin, porcine calcitonin, human calcitonin; cholecystokinin (CCK) and CCK agonists, CCK-8; cromolyn sodium (sodium or disodium chromoglycate); CPHPC; cyclosporine; desferrioxamine (DFO); erythropoietin; exedin and exedin agonists, exendin-3, exendin-4; filgrastim; follicle stimulating hormone (recombinant and natural); gallium nitrate; glucagon; glucagon-like peptide 1 (GLP-1), glucagon, glucagon-like peptide 2 (GLP-2); glucocerebrosidase; gonadotropin releasing hormone; growth hormone releasing factor; growth hormone releasing hormones; growth hormone, human growth hormone (hGH), recombinant human growth hormone (rhGH), bovine growth hormone, porcine growth hormone; heparin, unfractionated heparin, heparinoids, dermatans, chondroitins, low molecular weight heparin, very low molecular weight heparin, ultra low molecular weight heparin, synthetic heparin, fondiparinux; insulin, porcine insulin, bovine insulin, human insulin, human recombinant insulin, optionally having counter ions selected from the group consisting of zinc, sodium, calcium and ammonium; insulin-like growth factor, IGF-1; interferons, α-interferon, β-interferon, omega interferon, γ interferon; interleukin-1; interleukin-2; interleukin-11; interleukin-21; leutinizing hormone and leutinizing hormone releasing hormone; leptin (OB protein); methyphenidate salt; monoclonal antibodies, retuxin, tnf-alpha soluble receptors; oxytocin; parathyroid hormone (PTH), PTH 1-34 and PTH 1-38; peptide YY (PYY), PYY agonists, PYY3-36; dipeptidyl peptidase IV (DPP-4) inhibitors; prostaglandins; protease inhibitors; somatostatin; thrombopoietin; vancomycin; vasopressin; vitamins; vaccines, anthrax vaccines, y. pestis vaccines, influenza vaccines, herpes vaccines; analogs, mimetics and polyethylene glycol-modified derivatives of any of the above compounds, and any combination thereof.

2. The composition of claim 1, wherein said delivery agent compound is selected from:

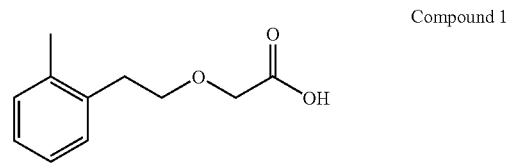

Compound 1

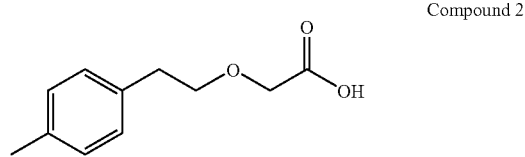

Compound 2

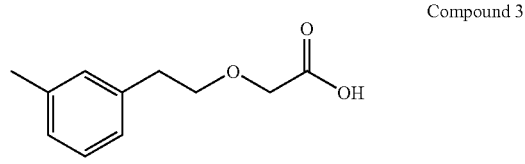

Compound 3

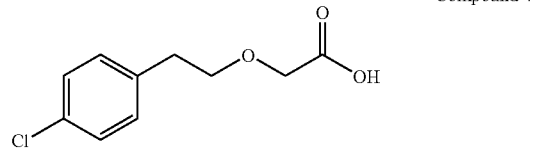

Compound 4

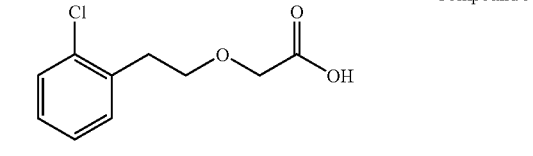

Compound 5

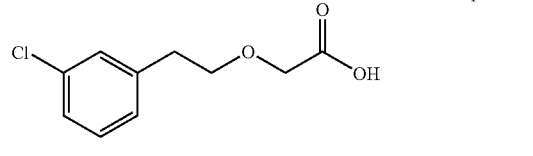

Compound 6

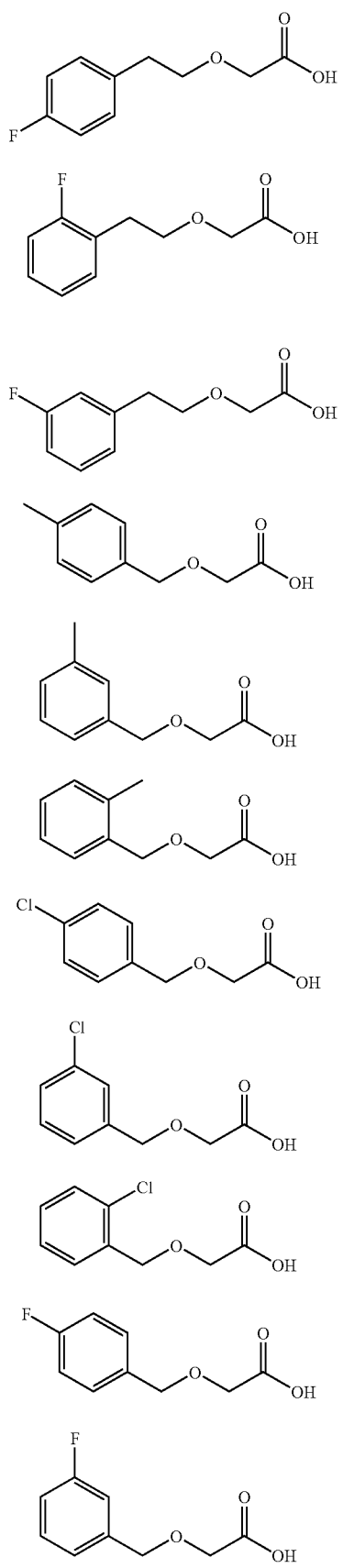
Compound 7
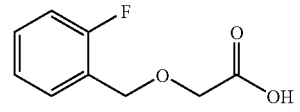 [SMILES: O=C(O)COCc1ccccc1F]
Compound 8
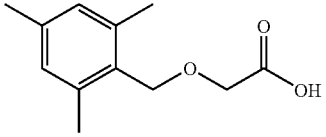
Compound 9
Compound 10
Compound 11
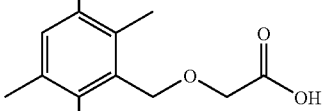
Compound 12
Compound 13
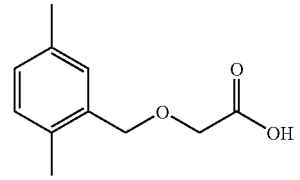
Compound 14
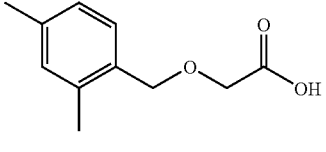
Compound 15
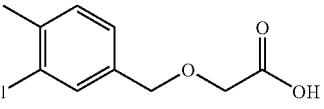
Compound 16
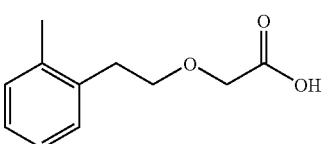
Compound 17
Compound 18
Compound 19
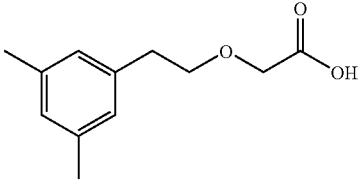
Compound 20
Compound 21
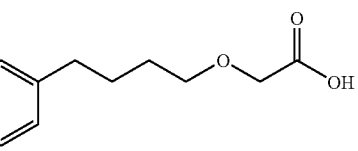
Compound 22
Compound 23
Compound 24
Compound 25
Compound 26
Compound 27
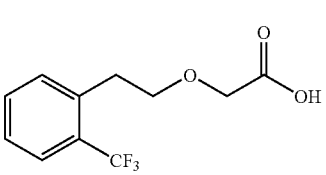 [SMILES: O=C(O)COCCc1ccccc1C(F)(F)F]

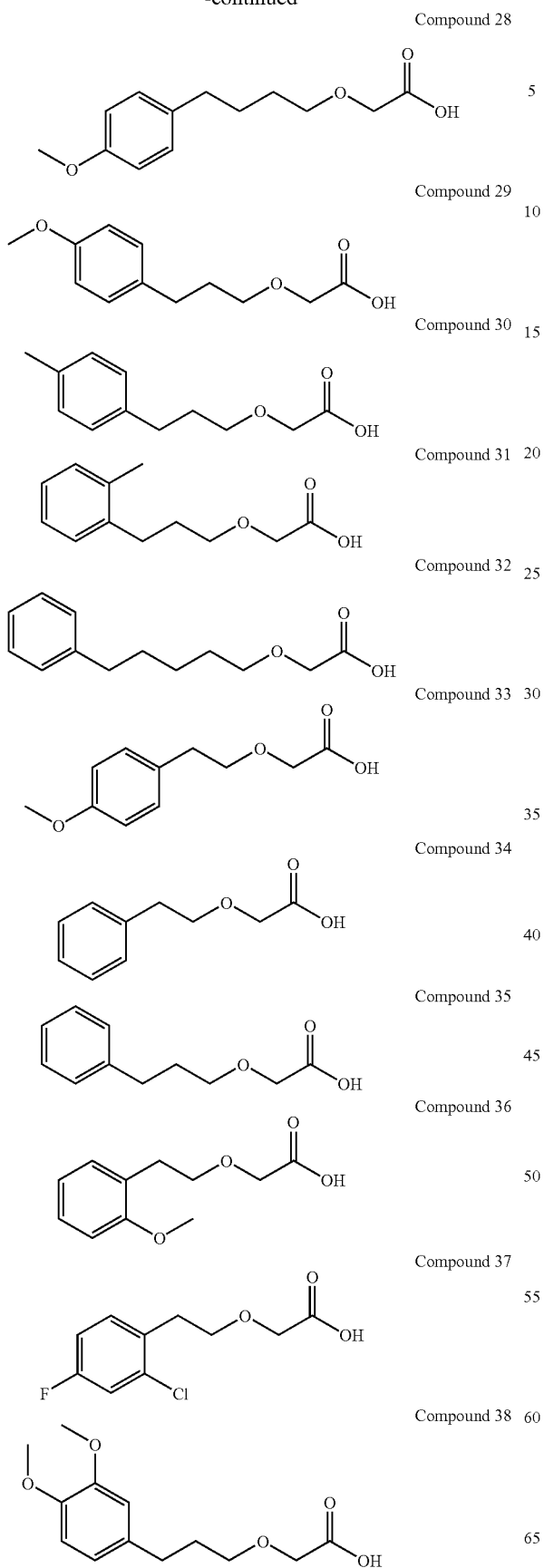
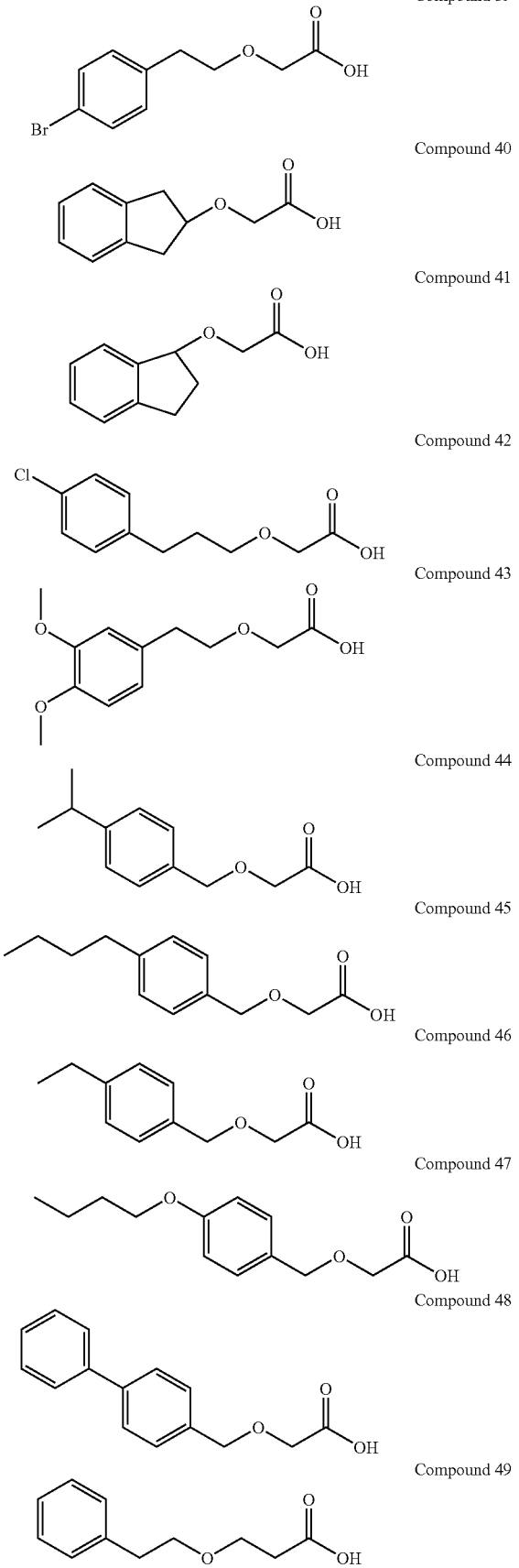

-continued

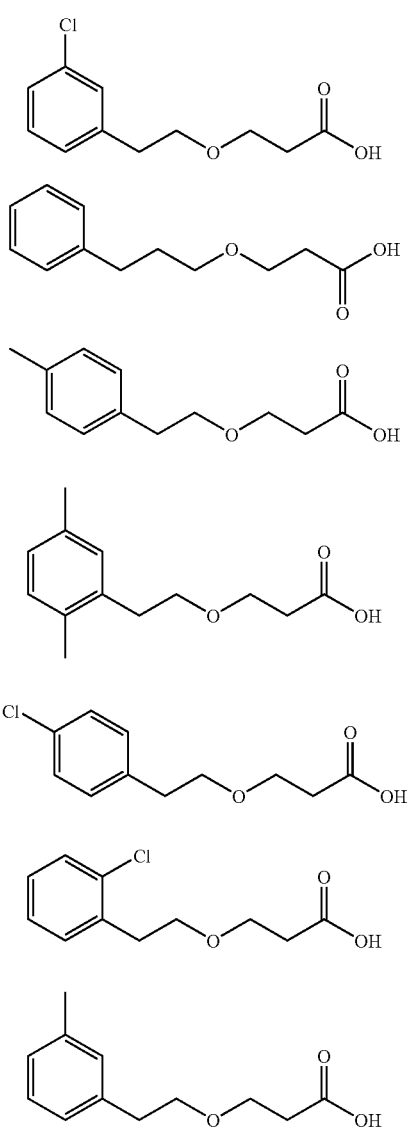

and pharmaceutically acceptable salts thereof.

3. The pharmaceutical composition of claim 1, wherein A is an unbranched and unsubstituted $C_1$-$C_6$ alkylene group.

4. The pharmaceutical composition of claim 1 wherein B is an unbranched and unsubstituted $C_1$-$C_2$ alkylene group.

5. The pharmaceutical composition of claim 1 wherein B is a methylene group.

6. The pharmaceutical composition of claim 1 wherein $R_1$, $R_2$, $R_3$, $R_4$ and $R_5$ are independently selected from H, halogen, substituted or unsubstituted alkyl, substituted or unsubstituted alkoxy or hydroxyl.

7. The pharmaceutical composition of claim 1 wherein at least one of $R_1$, $R_2$, $R_3$, $R_4$ and $R_5$ is a methyl, chlorine, fluorine, methoxy, bromine, 1-methylethyl, butyl, ethyl, —$OC_4H_9$, or phenyl.

8. The pharmaceutical composition of claim 1 wherein at least one of $R_1$, $R_2$, $R_3$, R and $R_5$ is methyl.

9. The pharmaceutical composition of claim 1 wherein at least one of $R_1$, $R_2$, $R_3$, $R_4$ and $R_5$ is chlorine.

10. The pharmaceutical composition of claim 1 wherein at least one of $R_1$, $R_2$, $R_3$, $R_4$ and $R_5$ is fluorine.

11. The pharmaceutical composition of claim 1 wherein at least one of $R_1$, $R_2$, $R_3$, $R_4$ and $R_5$ is methoxy.

12. The pharmaceutical composition of claim 1 wherein at least one of $R_1$, $R_2$, $R_3$, $R_4$ and $R_5$ is bromine.

13. The pharmaceutical composition of claim 1 wherein at least one of $R_1$, $R_2$, $R_3$, $R_4$ and $R_5$ is 1-methylethyl.

14. The pharmaceutical composition of claim 1 wherein at least one of $R_1$, $R_2$, $R_3$, $R_4$ and $R_5$ is butyl.

15. A compound selected from:

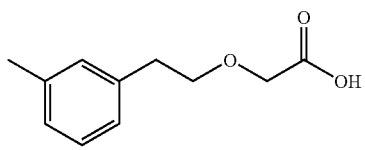

Compound 3

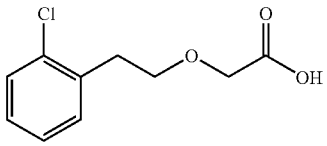

Compound 5

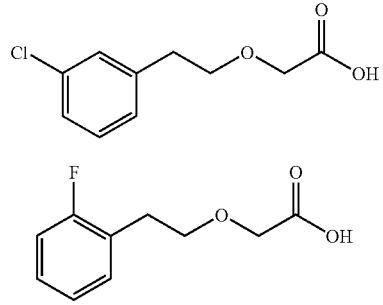

Compound 6

Compound 8

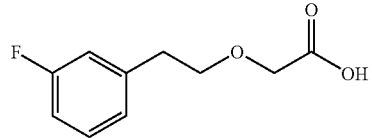

Compound 9

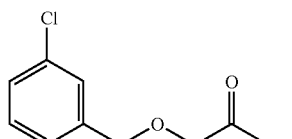

Compound 12

Compound 14

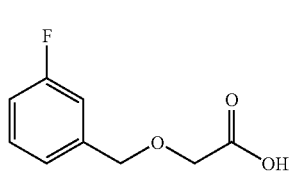

Compound 15

Compound 17

Compound 18
Compound 20
Compound 21
Compound 23
Compound 24
Compound 25
Compound 26
Compound 27
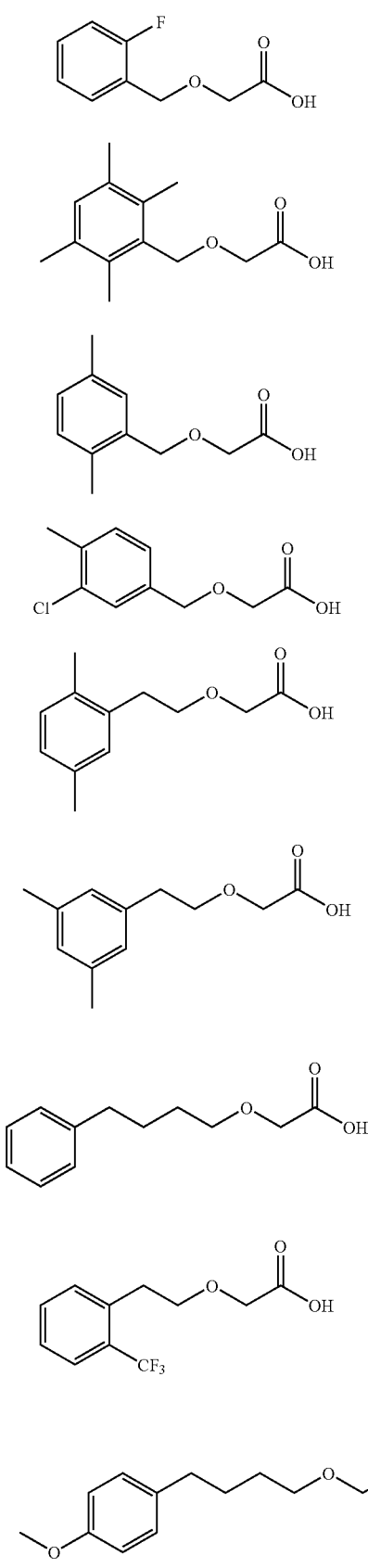
Compound 29
Compound 30
Compound 31
Compound 32
Compound 36
Compound 37
Compound 38
Compound 39
Compound 42
Compound 43
Compound 28
Compound 44
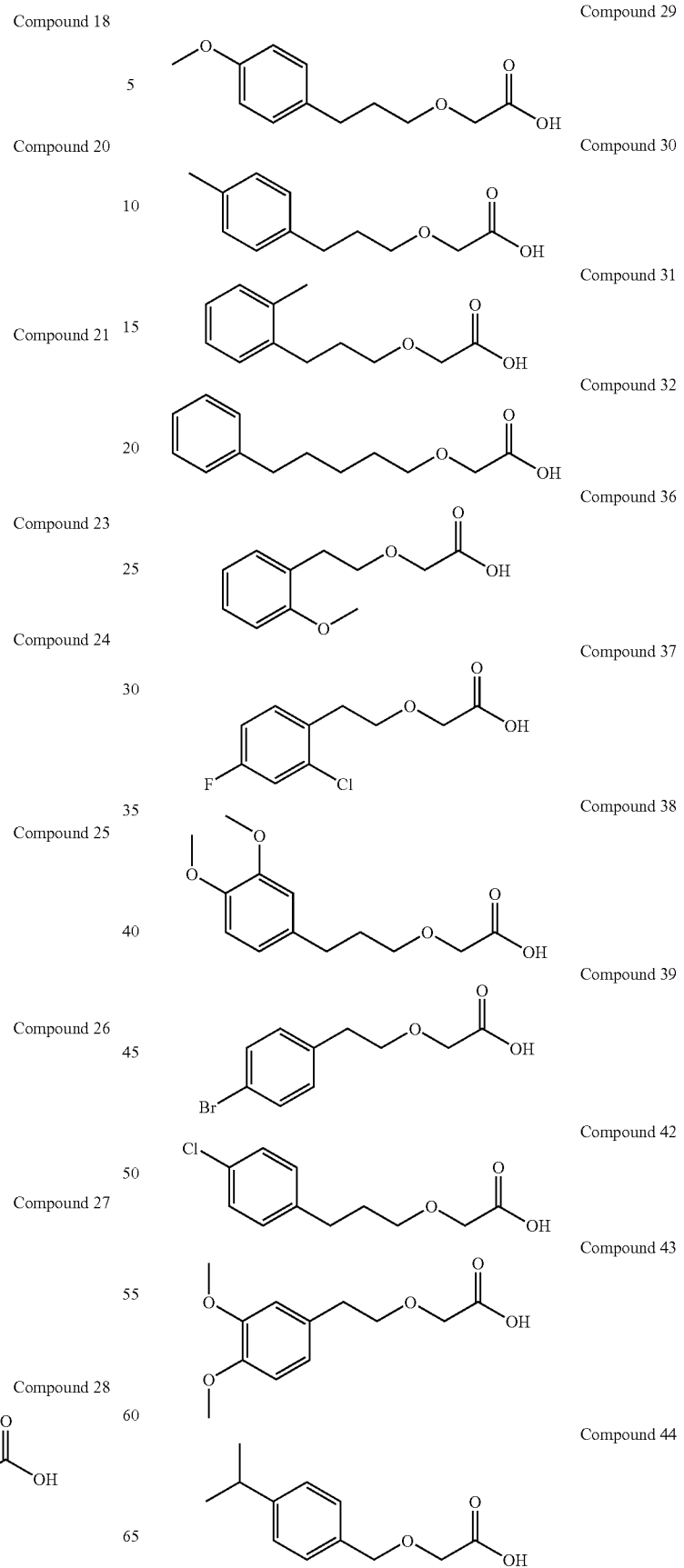

-continued

Compound 45
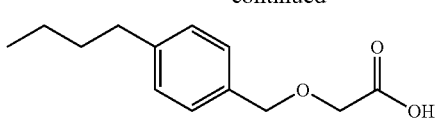

Compound 46
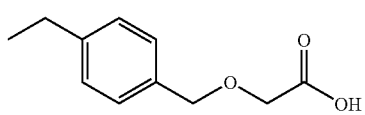

Compound 47
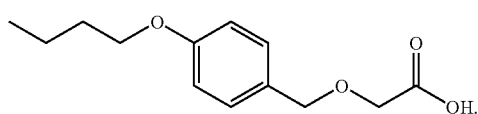 [SMILES: CCCCOc1ccc(COCC(=O)O)cc1]

Compound 52
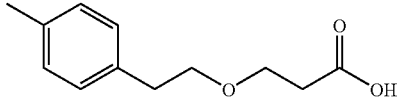

-continued

Compound 53
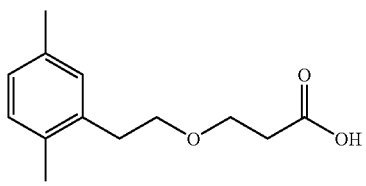 [SMILES: Cc1ccc(C)c(CCOCCC(=O)O)c1]

and pharmaceutically acceptable salts thereof.

16. The pharmaceutical composition of claim 1, wherein said biologically active agent comprises insulin, unfractionated heparin, low molecular weight heparin, very low molecular weight heparin, ultra low molecular weight heparin, calcitonin, parathyroid hormone, erythropoietin, daptomycin, human growth hormones, analogs, mimetics or polyethylene glycol-modified derivatives of these compounds, or any combination thereof.

17. A method for administering a biologically active agent to an animal in need of the agent, the method comprising administering orally to the animal the pharmaceutical composition of claim 1.

18. A method for preparing a pharmaceutical composition of claim 1, comprising mixing:
(A) at least one biologically active agent;
(B) at least one delivery agent compound of Formula I; and
(C) optionally, a dosing vehicle.

* * * * *